United States Patent
Yamazaki et al.

(10) Patent No.: US 8,932,460 B2
(45) Date of Patent: *Jan. 13, 2015

(54) PREPARATIVE SEPARATION/PURIFICATION SYSTEM

(75) Inventors: Tomoyuki Yamazaki, Kyoto (JP); Przemyslaw Stasica, Hertfordshire (GB); Bob Boughtflower, Hertfordshire (GB)

(73) Assignee: Shimadzu Corporation, Kyoto-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/024,701

(22) Filed: Feb. 10, 2011

(65) Prior Publication Data

US 2011/0198272 A1 Aug. 18, 2011

(30) Foreign Application Priority Data

Feb. 15, 2010 (JP) ................................ 2010-029889

(51) Int. Cl.
*G01N 30/34* (2006.01)
*G01N 30/08* (2006.01)
(Continued)

(52) U.S. Cl.
CPC ................ *G01N 30/34* (2013.01); *G01N 30/08* (2013.01); *G01N 30/26* (2013.01); *G01N 30/32* (2013.01);
(Continued)

(58) Field of Classification Search
CPC ....... G01N 30/82; G01N 30/08; G01N 30/26; G01N 30/32; G01N 30/34; G01N 30/80; G01N 2030/8494; G01N 30/20; G01N 30/462; G01N 2030/085; G01N 2030/202; G01N 2030/8411; G01N 2030/8429; B01D 15/163; B01D 15/247; B01D 15/166
USPC ............... 210/198.2, 656, 101, 143; 73/61.53
See application file for complete search history.

(56) References Cited

U.S. PATENT DOCUMENTS 8,607,620 B2 * 12/2013 Kono et al. .................. 73/61.53

2009/0314716 A1 12/2009 Osaka ......................... 210/656
2010/0281958 A1 * 11/2010 Kono et al. .................. 73/61.53

FOREIGN PATENT DOCUMENTS

JP 02-122260 5/1990
WO WO 2009/044425 A1 4/2009
(Continued)

OTHER PUBLICATIONS

Extended European Search report for counterpart European Application No. 11154118.1.
(Continued)

*Primary Examiner* — Ernest G Therkorn
(74) *Attorney, Agent, or Firm* — Morgan, Lewis & Bockius LLP (57) ABSTRACT

The present invention aims at providing a preparative separation/purification system for vaporizing an eluate in a short period of time, while enhancing the efficiency of collecting the target substance by accelerating the initiation of collecting the eluate. The preparative separation/purification system in which water containing a target component is passed through a column 8 to capture the target component in the column 8 and then a solvent is passed through it to collect the target compound, includes: a liquid supply means 7 for supplying a solvent to the column 8, with the target component captured in the column 8, while the column 8 is vertically held with the inlet end thereof directed downwards and the discharge end thereof directed upwards, the solvent having a low solubility to water and having a specific gravity greater than that of water; a passage selection means 12 for changing the passage configuration so that a solution exiting from the column 8 is selectively sent to either a collection passage 13 or a disposal passage 14; a passage control means 30 for controlling the passage selection means 12 so that, when water exits from the column 8, the water is sent to the disposal passage 14, and when solution containing solvent exits from the column 8, the solution is sent to the collection passage 13; and a flow rate control means 30 for controlling so that the water is supplied at a first flow rate to the disposal passage 14, and the solution containing solvent is supplied to the collection passage 13 at a flow rate lower than the first flow rate.

9 Claims, 3 Drawing Sheets

(51) Int. Cl.
  *G01N 30/26* (2006.01)
  *G01N 30/32* (2006.01)
  *G01N 30/80* (2006.01)
  *G01N 30/82* (2006.01)
  *B01D 15/16* (2006.01)
  *B01D 15/24* (2006.01)
  *G01N 30/20* (2006.01)
  *G01N 30/46* (2006.01)
  *G01N 30/84* (2006.01)

(52) U.S. Cl.
  CPC ............... *G01N 30/80* (2013.01); *G01N 30/82* (2013.01); *B01D 15/163* (2013.01); *B01D 15/166* (2013.01); *B01D 15/247* (2013.01); *G01N 30/20* (2013.01); *G01N 30/462* (2013.01); *G01N 2030/085* (2013.01); *G01N 2030/202* (2013.01); *G01N 2030/8411* (2013.01); *G01N 2030/8429* (2013.01); *G01N 2030/8494* (2013.01)

USPC ......... 210/198.2; 210/101; 210/143; 210/656

(56) References Cited

FOREIGN PATENT DOCUMENTS

WO  WO 2009/044426 A1  4/2009
WO  WO 2009/044427 A1  4/2009

OTHER PUBLICATIONS

Japanese Office Action mailed on Jun. 4, 2013 for the correspondence Japanse Patent Application No. 2010-029889.
English translation of "Reason for Rejection" of Japanese Office Action dated Jun. 4, 2013 for Japanese Patent App. No. 2010-029889.
Examination Report received for European Patent Application No. 11154118.1 mailed Nov. 10, 2014, 4 pages.

* cited by examiner

Fig. 1

PREPARATIVE SEPARATION/PURIFICATION SYSTEM

The present invention relates to a preparative separation/purification system for separately extracting one or more components from a solution by a liquid chromatograph, and purifying and collecting the components in solid forms.

BACKGROUND OF THE INVENTION

Conventionally, in the pharmaceutical industry and other fields, preparative separation/purification systems utilizing chromatographs are used to analyze synthesized compounds or store them in a library (Refer to Japanese Unexamined Patent Application Publication No. H02-122260).

In these apparatuses, target components (compounds) in a sample solution are temporally separated by a liquid chromatograph. The separated target components are then respectively introduced into different trap columns and temporarily captured therein. Subsequently, a solvent is supplied into each trap column to quickly elute the component from the trap column and collect it in a container. Thus, a plurality of solutions each containing one target component at a high concentration are collected in respective containers. These separately collected solutions are then subjected to a vaporizing and drying process to remove the solvent and collect the target components in solid forms. The vaporizing and drying process normally includes heating the collected eluate or centrifuging them under a vacuum.

According to the aforementioned method, however, a single vaporizing and drying process requires a long period of time of for example, several hours to one day. In the pharmaceutical industry, various efforts have been made to improve the efficiency of searching for a large number of synthetic compounds for medicinal compounds; for example, the analysis time has been reduced by using faster analysis apparatuses or optimizing the analytical methods. Reducing the time required for the vaporizing and drying process is a critical issue since this process consumes, within the entire process, the longest period of time.

One reason that a long period of time is required to vaporize the solvent from the eluate collected is the presence of water included in the collected eluate. As the solvent for eluting target components captured in a trap column, an organic solvent is often used. As compared to water, organic solvents have much lower boiling points and hence are highly volatile. Therefore, when the target components are dissolved in a pure organic solvent, the vaporizing and drying process requires only a short period of time. On the other hand, if water, which is less volatile, is included in the solvent, the vaporizing and drying process takes a considerably longer period of time.

When the target component is introduced into the trap column with the mobile phase and captured therein, in many cases, the mobile phase consists of either water or an aqueous solvent containing water as the main component. In these cases, a certain amount of water remains in the trap column at the completion of capturing the target component. This problem also arises in the widely used technique of introducing water into the passage of the mobile phase at a location before the trap column in order to dilute the mobile phase with water and thereby reduce the elution power of the mobile phase so that the target component can be assuredly captured. In this case, the water remains in the trap column at the completion of capturing the target component. Furthermore, after the target component is captured, it is often necessary to wash the trap column by introducing water into it to remove unnecessary components other than the target one, such as the salts originating from the mobile phase, that are present within the trap column. In this case, the mobile phase in the trap column is replaced with water, so that the trap column becomes filled with the water.

For such a variety of reasons, in many cases, the trap column contains a considerable amount of water after the target component is captured. When such a large amount of water is present in the trap column, supplying an organic solvent into the trap column to elute the target component will naturally result in a large amount of remnant water to be included in the solution exiting from the trap column. If both water and an organic solvent are contained in the collected solution, a long period of time is required to vaporize the water, and what is worse, the water overlies the organic solvent stored in the collection container as a cover, which prevents the organic solvent from evaporating.

To solve this problem, a preparative separation/purification system has been developed which is capable of removing water and other unwanted residual solvents from a trap column in a short period of time before a target component captured in a trap column is eluted from the column (International Publication No. WO2009/044426). In this preparative separation/purification system, a second solvent is supplied from the lower end of the trap column, with the target component held in the trap column. The second solvent has a specific gravity greater than the specific gravity of a first solvent (water or an aqueous solvent) remaining in the trap column and has a low solubility to the first solvent. Consequently, the first solvent is pushed up by the second solvent and discharged from the trap column. By disposing of this first solvent, the first solvent is removed from the trap column. In this manner, the preparative separation/purification system of International Publication No. WO2009/044426 can collect an eluate consisting of a water-free organic solvent with the target component dissolved therein. Hence, the solvent in this eluate can be vaporized in a short period of time to obtain the target component in dry, solid forms.

SUMMARY OF THE INVENTION

In the separation/purification system disclosed in International Publication No. WO2009/044426, the second solvent, which has a low solubility to the first solvent, pushes up the first solvent. Although the second solvent and the first solvent are insoluble with each other, they partly form an emulsion around the interface between them. Since this emulsion contains the first solvent, in the system of International Publication No. WO2009/044426, the emulsion discharged from the upper end of the trap column is entirely disposed of, and only the second solvent is collected. This method can effectively prevent water from being included in the collection container, so that the eluate containing the target component is efficiently vaporized and dried.

However, the target compound which is captured by the adsorbent in the trap column also dissolves in the second solvent in the emulsion. That is, the emulsion that is discharged from the trap column also contains the target compound. Therefore, if the emulsion is completely disposed of, the collection efficiency will be decreased particularly in the case where the amount of the target compound collected in the trap column is small.

The present invention has been developed in view of the aforementioned problem, and the objective thereof is to provide a preparative separation/purification system for efficiently performing the process of vaporizing and drying the eluate containing a target compound, while enhancing the collection efficiency of the target compound by accelerating the initiation of collecting the eluate.

To solve the previously described problems, the first aspect of the present invention provides a preparative separation/purification system in which a solution containing a target component is passed through a trap column to capture the target component in the trap column and then a solvent having an elution capability is passed through the trap column to elute the target component from the trap column and collect the target component, which is characterized by including:

a) a holding means for holding the trap column so that an internal passage of the trap column vertically extends with an inlet end thereof directed downwards and a discharge end thereof directed upwards;

b) a liquid supply means for supplying a second solvent to the inlet end of the trap column, with the target component captured in the trap column held by the holding means, the second solvent having a low solubility to a first solvent remaining in the trap column and having a specific gravity greater than a specific gravity of the first solvent;

c) a passage selection means for changing a passage configuration so that a solution exiting from the discharge end of the trap column is selectively sent to either a collection passage leading to a collection container or a disposal passage leading to a disposal port;

d) a passage control means for controlling the passage selection means so that the first solvent extruded from the discharge end of the trap column by a push of the second solvent is sent to the disposal passage according to the action of supplying the second solvent to the trap column by the liquid supply means, while the solution with the second solvent contained therein is sent to the collection passage at the timing when the solution exits from the discharge end of the trap column; and e) a flow rate control means for controlling the liquid supply means so that the second solvent is supplied at a first supply flow rate when the first solvent is sent to the disposal passage from the discharge end of the trap column, while the second solvent is supplied at a second supply flow rate which is lower than the first supply flow rate when the solution with the second solvent contained therein is sent to the collection passage from the discharge end of the trap column.

The first solvent is either a mobile phase used in a liquid chromatograph for separating a target component from a solution containing miscellaneous components, or a cleaning liquid for washing or cleaning the inner passage of the column after the target component is captured in the trap column. Normally, water or an aqueous solvent containing water is used as the main component. The second solvent satisfies the aforementioned requirements for the first solvent relating to the low solubility and specific gravity, and may be an organic solvent consisting of either dichloromethane (specific gravity: 1.32) or a mixed liquid containing dichloromethane. The mixed liquid is a solvent in which, for example, methanol is mixed to control its elution capability or the solubility of the compound.

The "timing when the solution with the second solvent contained therein exits from the discharge end of the trap column" is the timing when the second solvent begins to be contained in the solution discharged from the discharge end of the trap column (or when an emulsion begins to be discharged), or around that time.

To solve the previously described problems, the second aspect of the present invention provides a preparative sepa ration/purification system according to the first aspect of the present system, further including:

f) a computation means for computing a period of time from a point in time when the second solvent begins to be sent to the trap column until the solution with the second solvent contained therein begins to be discharged from the discharge end of the trap column, the period of time being computed from an internal volume of the trap column and the first supply flow rate, wherein:

the passage control means controls the passage selection means, when the period of time computed by the computation means has elapsed, in such a manner that the solution with the second solvent contained therein exiting from the discharge end of the trap column is sent to the collection passage.

To solve the previously described problems, the third aspect of the present invention provides a preparative separation/purification system according to the first aspect of the present system, further including:

g) a collection passage switching time setting means for allowing a user to set a period of time from a point in time when the second solvent begins to be sent to the trap column until the solution with the second solvent contained therein begins to be discharged from the discharge end of the trap column, wherein:

the passage control means controls the passage selection means, when the period of time set by the collection passage switching time setting means has elapsed, in such a manner that the solution with the second solvent contained therein exiting from the discharge end of the trap column is sent to the collection passage.

To solve the previously described problems, the fourth aspect of the present invention provides a preparative separation/purification system according to the first aspect of the present system, further including:

h) a discharged solution discrimination means for determining whether or not the solution discharged from the discharge end of the trap column contains the second solvent, wherein:

the passage control means controls the passage selection means, when the discharged solvent discrimination means has determined that the discharged solution contains the second solvent, in such a manner that the solution with the second solvent contained therein exiting from the discharge end of the trap column is sent to the collection passage.

To solve the previously described problems, the fifth aspect of the present invention provides a preparative separation/purification system according to any one of the first through fourth aspects of the present system, further including:

i) a disposal passage switching time setting means for allowing a user to set a period of time after the elapse of which the passage selection means changes the passage configuration so that the passage of the solvent is changed from the collection passage to the disposal passage after the second solvent exiting from the trap column is sent to the collection passage, wherein:

the passage control means controls the passage selection means, when the period of time set by the disposal passage switching time setting means has elapsed, in such a manner that the solution exiting from the trap column is sent to the disposal passage.

To solve the previously described problems, the sixth aspect of the present invention provides a preparative separation/purification system according to the fifth aspect of the present system, wherein the period of time set by the disposal passage switching time setting means is a period of time required for the target component captured in the trap column to be completely eluted by the second solvent.

To solve the previously described problems, the seventh aspect of the present invention provides a preparative separation/purification system according to the fifth aspect of the present system, wherein the period of time set by the disposal passage switching time setting means is a period of time required for a drying of the target component contained in the solution collected in the collection container to be completed.

To solve the previously described problems, the eighth aspect of the present invention provides a preparative separation/purification system according to any one of the first through seventh aspects of the present system, further including:

j) a heater for heating the collection container; and k) a gas supplier for forming a flow of gas to scatter the discharged solution which is dripped or flowed into the collection container.

For the aforementioned gas, an inert gas is preferable. For example, helium, argon, and nitrogen are available.

To solve the previously described problems, the ninth aspect of the present invention provides a preparative separation/purification system according to any one of the first through eighth aspects of the present system, wherein:

the liquid supply means supplies either the second solvent or a third solvent to the inlet end, of the trap column, and the preparative separation/purification system further includes:

l) a solvent selection means for changing a kind of a solution supplied by the liquid supply means to either the second solvent or the third solvent for washing the trap column;

m) a third solvent switching time setting means for allowing a user to set a period of time for the solvent selection means to change the solvent to the third solvent from the second solvent; and n) a solvent control means for controlling the solvent selection means, when the period of time set by the third solvent switching time setting means has elapsed, to change the solvent supplied to the liquid supply means to the third solvent from the second solvent.

The third solvent is a solvent suitable for rinsing the trap column, such as acetonitrile. Accordingly, the second solvent is replaced with the third solvent in the trap column to make the trap column ready for the next analysis.

In the preparative separation/purification system according to the present invention, the second solvent having a low solubility to the first solvent pushes up the first solvent, so that an emulsion is formed at the boundary between the second solvent and the first solvent. In the preparative separation/purification system according to the first aspect of the present invention, the discharged solution begins to be collected at the timing when the solution with the second solvent contained therein exits from the discharge end of the trap column, i.e. at the timing when the emulsion begins to be discharged from the trap column. Since the target component has dissolved in the second solvent in the emulsion, such a configuration can increase the collection efficiency of the target component.

If the collection is initiated a little while before an emulsion is formed, the second solvent can be completely collected, which can assuredly increase the collection efficiency of the target component. In the case where the collection is initiated a little while after an emulsion is formed, although the second solvent initially discharged from the trap column cannot be collected, the amount of emulsion collected in the collection container is decreased. As a result, the amount of the first solvent (water) is decreased, which allows an efficient and rapid vaporization process of the solvent in the collection container.

In addition, in the preparative separation/purification system according to the first aspect of the present invention, the second solvent is supplied, at the timing when the solution with the second solvent contained therein exits from the discharge end of the trap column, at a flow rate which is lower than the flow rate at which the first solvent exiting from the trap column is sent to the disposal passage. With this configuration, the amount of emulsion which flows into the collection container per unit time can be decreased. This allows the solvent in the collection container to vaporize in a shorter period of time than in a conventional system.

Changing the flow rate of the second solvent to a lower flow rate at the timing when the emulsion is discharged from the trap column can also solve the problem that the target component deposits in the trap column or the passage and clogs the passage. This problem can occur in the case where the compound dissolved in the solvent has poor water solubility. The compound deposits when it comes into contact with the water, and the deposit clogs the channel. In the preparative separation/purification system according to the present invention, a low supply flow rate is set while the emulsion of the first solvent and the second solvent is discharged from the trap column. Therefore, the degree of muddling of the first solvent and the second solvent in the emulsion is suppressed. This suppresses the probability that the target compound dissolved in the second solvent in the emulsion contacts with the first solvent (water), suppressing the deposition of the target compound while the solvents are flowing through the passage.

In the preparative separation/purification system according to the fifth aspect of the present invention, a user sets a period of time when the passage selection means changes the passage configuration so that the passage of the solvent is changed from the collection passage to the disposal passage after the second solvent exiting from the trap column is sent to the collection passage. When the specified period of time has elapsed, the solution exiting from the trap column is sent to the disposal passage. Hence, even in the case where it is desirable to terminate the collection operation while the target component captured in the trap column still remains in the column, the solvent is continued to be sent to the collection passage until the period of time has elapsed which is required for the target component captured in the trap column to be completely eluted by the second solvent (in the sixth aspect of the present invention) or until the period of time has elapsed which is required to terminate the vaporization and drying of the solvent in the collection container and to complete the drying of the target component (in the seventh aspect of the present invention). The continued supply of the solvent decreases the amount of target component remaining within the collection passage, suppressing the probability that the target component deposits within the collection passage after the supply of the solvent is halted. In the meantime, such configurations do not adversely affect the efficiency of the drying process of the target component because the flow rate of the solvent supplied into the collection container is set to be low and the supplied solvent is a highly-volatile organic solvent.

Furthermore, in the preparative separation/purification system according to the eighth aspect of the present invention, the gas supplier forms a flow of gas, which scatters the solution dripped or flowed into the collection container, and the solution is atomized apart. The fine droplets which have flown in all directions adhere to the inner wall of the container. Since the container is heated by the heater, the solvent in the droplet immediately vaporizes, leaving the target component deposited on the inner wall of the container. If much water is contained in the solution, the solvent in the droplet may not completely vaporize; it may flow down the inner wall to deposit on the bottom of the container. The aforementioned flow of gas can be powerfully supplied at this solution on the bottom of the container, whereby the vaporization of the solvent is further accelerated.

In the preparative separation/purification system according to the ninth aspect of the present invention, when the period of time set by the user has elapsed, the solvent is changed from the second solvent to the third solvent for washing the column, which is supplied to the trap column. Accordingly, the trap column is washed to be ready for the next analysis.

EXPLANATION OF THE NUMERALS

1 ... Solution Container
2 ... Wash Water Container
3 ... Eluting Solvent Container
4 ... Wash Solution Container
5 ... Selector Valve
6 ... Supply Passage
7 ... Pump
8 ... Trap Column
9 ... Column Rack
10 ... Discharge Passage
11 ... Fraction Collector Head
12 ... Two-Way Selector Valve
13 ... Preparative Separation Passage
14 ... Disposal Passage
15 ... Gas Passage
16 ... On/Off Valve
17 ... Collection Container
18 ... Container Rack
19 ... Heater
20 ... Temperature Sensor
21 ... Temperature Regulator
30 ... Controller
31 ... Operation Unit

DETAILED DESCRIPTION OF A PREFERRED EMBODIMENT

An embodiment of the preparative separation/purification system according to the present invention will be described with reference to FIGS. 1 through 5.

Figure 1:
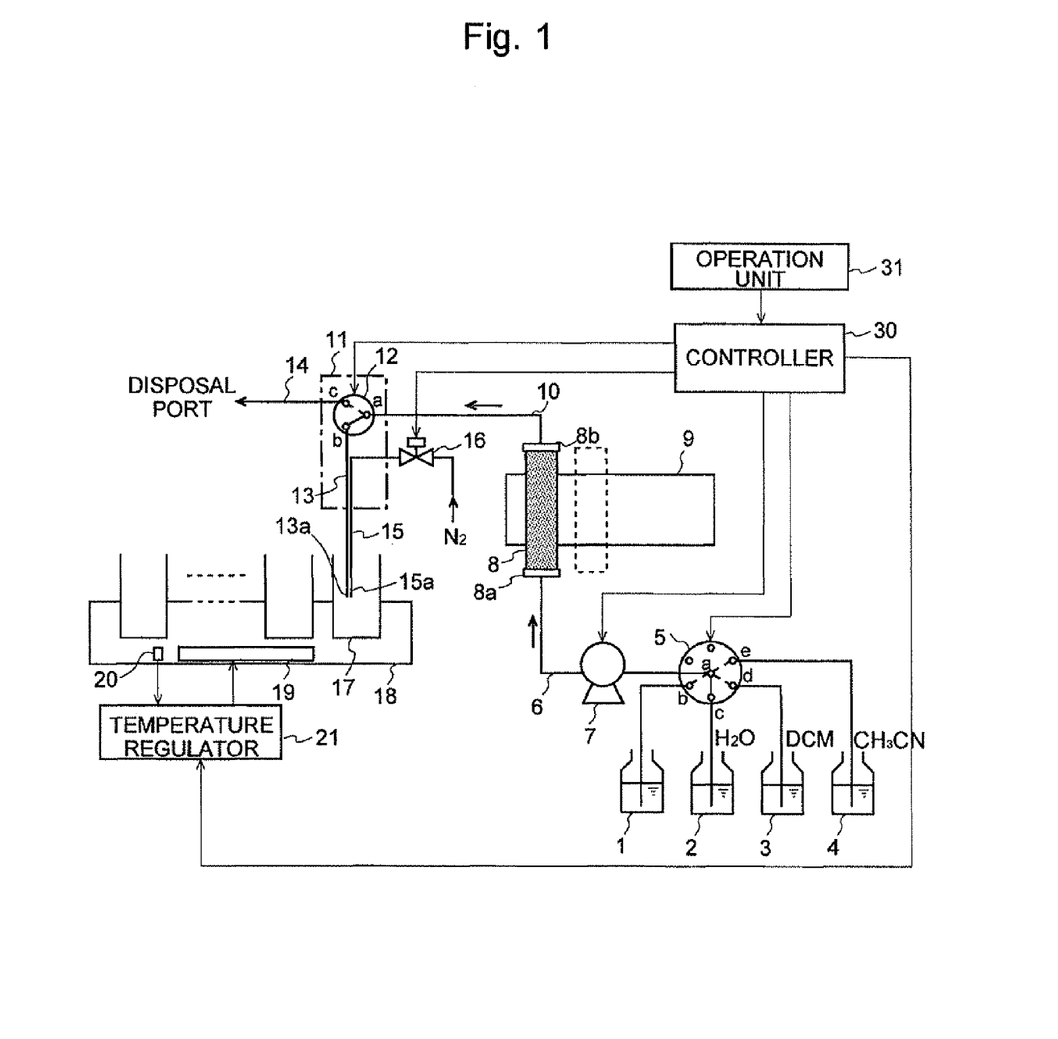
FIG. 1 is a schematic configuration diagram of a preparative separation/purification system according to an embodiment of the present invention.

FIG. 1 is a schematic configuration diagram of the preparative separation/purification system of the present embodiment. In FIG. 1, a mobile phase with the target compound dissolved therein is contained in a solution container 1. A wash water container 2 holds pure water acting as the first solvent of the present invention. An eluting solvent container 3 holds dichloromethane/methanol mixture (hereinafter, which will be simply referred to as "dichloromethane" and which is labeled as "DCM" in the figure) acting as the second solvent of the present invention. A wash solution container 4 holds acetonitrile acting as the third solvent of the present invention. A selector valve 5 is provided to change the passage configuration so that one of the liquids held in these containers 1 through 4 is selectively supplied to a supply passage 6 on which a pump 7 for drawing a liquid at a predetermined flow rate is provided.

A trap column 8 is 20 mm in internal diameter and 30 mm in height. The diameter of the hole is 0.8 mm. The trap column 8 is filled with an adsorbent for capturing the target compound. The trap column 8 is held in a substantially vertical position by a column rack 9, which corresponds to the holding means of the present invention. The inlet end 8a, to which the aforementioned supply passage 6 is connected, is directed downwards, while the outlet end 8b, to which a discharge passage (to be described later) 10 is connected, is directed upwards. Although FIG. 1 shows only one trap column 8, it is possible to hold two or more trap columns by the column rack 9, side by side, as indicated by the dotted line in FIG. 1.

A discharge passage 10 has one end connected to the outlet end 8b of the trap column and the other end to port a of a two-way selector valve 12 embedded in a preparative separation head 11. A preparative separation passage 13 is connected to port b of the selector valve 12, while a disposal passage 14 leading to a disposal port is connected to port c. The two-way selector valve 12 connects either the preparative separation passage 13 or the disposal passage 14 to the discharge passage 10. The other end of the preparative separation passage 13 is a solution nozzle 13a for dripping the supplied solution. A gas ejection nozzle 15a at the end of a gas passage 15 is located close to the solution nozzle 13a. An on/off valve 16 is provided on the gas passage 15. When the on/off valve 16 is opened, a nitrogen gas supplied from a gas cylinder or similar source (not shown) is ejected from the gas ejection nozzle 15a. The solution nozzle 13a and the gas ejection nozzle 15a may have a double-tube structure.

A plurality of collection containers 17 for collecting the separated and purified target compounds are held in a container rack 18. The container rack 18 is provided with a heater 19 and a temperature sensor 20. Based on the temperature monitored with the temperature sensor 20, a temperature regulator 21 regulates the heating current supplied to the heater 19 so that the collection containers 17 can be heated to appropriate temperatures. The preparative separation head 11, which can be moved in both horizontal and vertical directions by a drive mechanism (not shown), is horizontally moved to a position above any one of the collection containers 17 held in the container rack 18 and then vertically lowered to insert the solution nozzle 13a and the gas ejection nozzle 15a into the selected collection container 17 so that a solution can be dripped into the same container.

Instead of moving the preparative separation head 11, it is also possible to move the container rack 18 so that a solution dripped from the solution nozzle 13a will fall into any one of the collection containers 17 held in the container rack 18.

A controller 30 including a central processing unit (CPU) and other components automatically performs a preparative separation/purification task by switching the valves 5 and 12, controlling the operation of the pump 7 (the flow rate or flow velocity), and setting a target temperature for the temperature regulator 21 according to a previously prepared program. An operation unit 31 allows users to enter the conditions and other information relating to the preparative separation/purification task.

Figure 2:
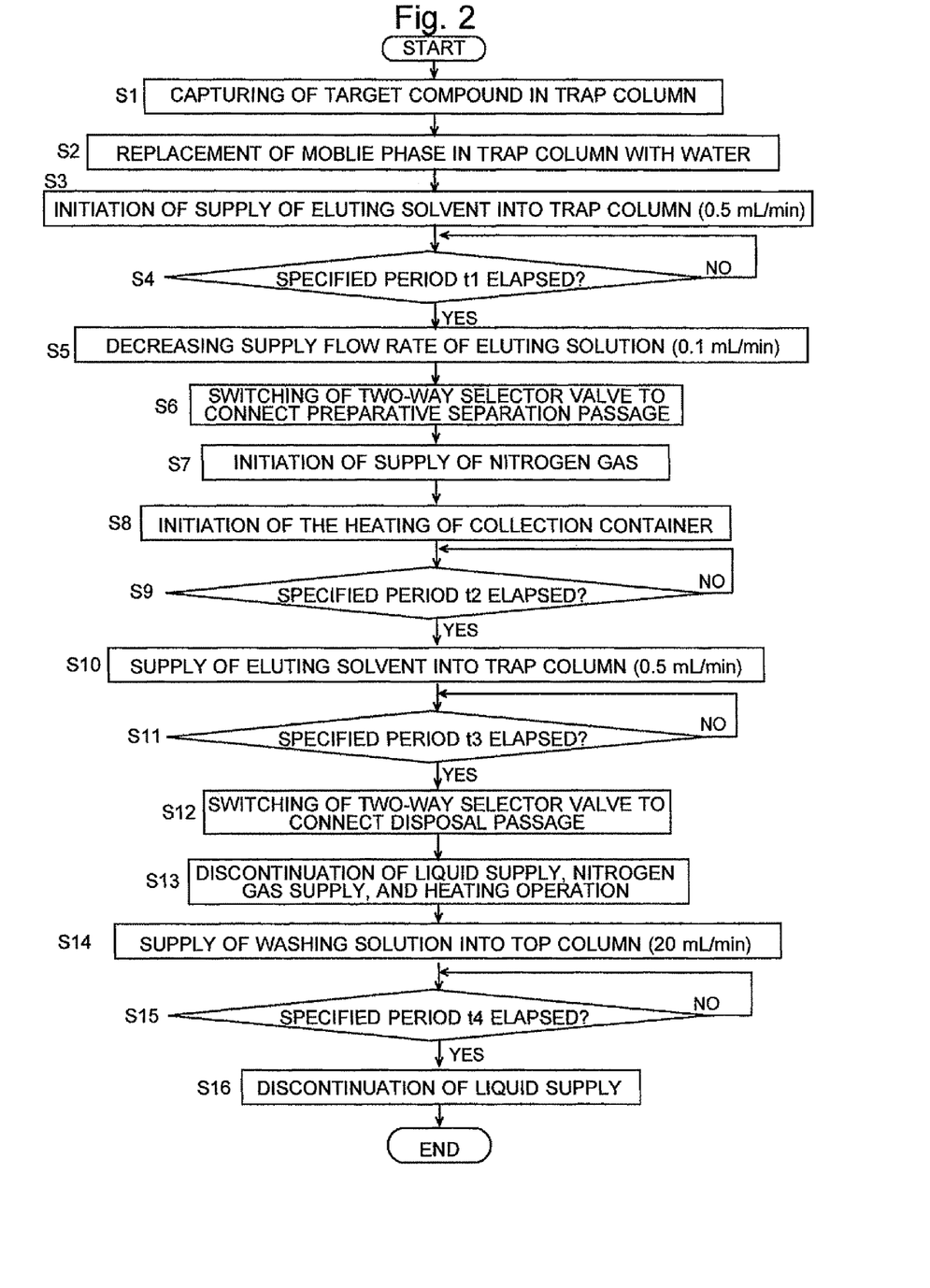
FIG. 2 is a control flowchart for an automatic preparative separation/purification in the preparative separation/purification system according to an embodiment of the present invention.
Figure 3:
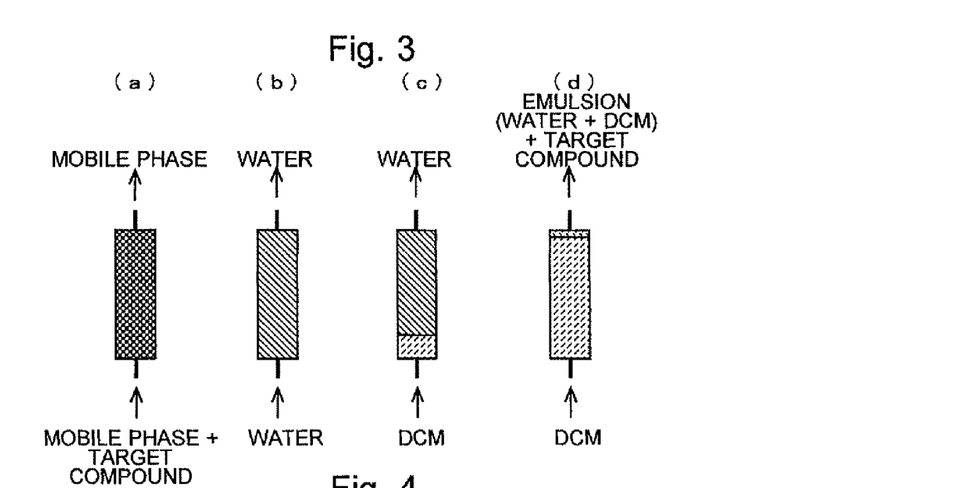
FIG. 3 is an explanation diagram for explaining how the solvent within a trap column changes during the preparative separation/purification operation according to the present invention.
Figure 4:
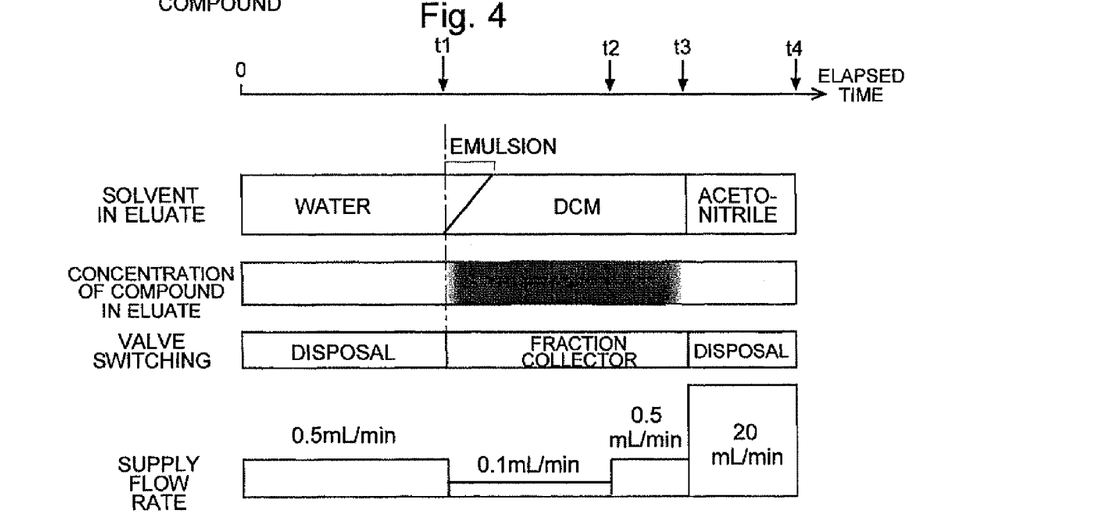
FIG. 4 is an explanation diagram showing how an eluate from the trap column changes during the preparative separation/purification operation according to the present invention.
Figure 5:
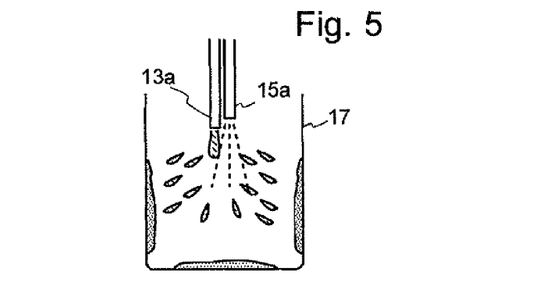
FIG. 5 is an explanation diagram showing a mechanism for vaporizing a solvent from the eluate collected by the preparative separation/purification system according to the present embodiment.

An automatic preparative separation/purification operation in the preparative separation/purification system of the present embodiment is hereinafter described with reference to FIGS. 2 to 5. FIG. 2 is a control flowchart for this automatic preparative separation/purification process, FIG. 3 is an explanation diagram for explaining how the solvent in the trap column 8 changes during the automatic preparative separation/purification operation, FIG. 4 is an explanation diagram showing how the solvent and target compound in an eluate from the trap column 8 change with time during the automatic preparative separation/purification operation, and FIG. 5 is an explanation diagram showing a mechanism for vaporizing the solvent from the collected eluate.

The controller 30 initially connects the solution container 1 (port b) and the supply passage 6 (port a) via the selector valve 5 and activates the pump 7 to supply the liquid at a predetermined constant flow rate. The controller 30 also connects the discharge passage 10 (port a) and the disposal passage 14 (port c) via the two-way selector valve 12. The pump 7 draws the solution from the solution container 1 and delivers it through the inlet end 8a into the trap column 8. Then, the target compound in the solution is captured by the adsorbent (Step S1; refer to FIG. 3(a)). The mobile phase from which the target compound has been removed exits from the outlet end 8b, to be disposed of via the discharge passage 10 and the disposal passage 14 to the disposal port.

After the solution is supplied into the trap column 8 for a predetermined period of time or until the solution prepared in the solution container 1 is exhausted, the controller 30 switches the selector valve 5 to connect the wash water container 2 (port c) and the supply passage 6 (port a). Then, the pump 7 draws pure water from the wash water container 2 and delivers it through the inlet end 8a into the trap column 8. By this process, any unwanted water-soluble substance (e.g. a salt) adhered to the adsorbent in the previous process of capturing the target component is removed from the inside of the trap column 8 (Step S2). As a result of supplying the pure water, the mobile phase stored in the trap column 8 immediately before the initiation of the water supply is replaced with water, and this water eventually fills the trap column 8, as shown in FIG. 3(b). The target compound captured on the adsorbent can barely elute into water. Therefore, at this point in time, the target compound is still captured in the trap column 8.

Next, the controller 30 switches the selector valve 5 to connect the eluting solvent container 3 (port d) and the supply passage 6 (port a). Then, the pump 7 draws dichloromethane from the eluting solvent container 3 and begins to introduce it through the inlet end 8a into the trap column 8 (Step S3). At this stage, the supply flow rate of the pump 7 is set at 0.5 mL/min. Dichloromethane has a specific gravity of 1.32, which is larger than that of water, and is not soluble to water. Therefore, when dichloromethane is introduced from the inlet end 8a of the trap column 8, it does not mix much with water present within the trap column 8, as shown in FIG. 3(c), and the interface between dichloromethane and water gradually rises. In other words, dichloromethane gradually accumulates from the bottom of the trap column while pushing water upwards. The pushed water overflows from the outlet end 8b at the upper end of the trap column 8 and flows through the two-way selector valve 12 and the disposal passage 14 and eventually reaches the disposal port.

Although dichloromethane and water are insoluble with each other, they partially form an emulsion at their interface. Therefore, as shown in FIG. 3(d), as the interface between water and dichloromethane comes closer to the upper end of the trap column 8, the eluate from the outlet end 8b of the trap column 8 changes from water to an emulsion (solution of dispersion system). Since dichloromethane has a strong elution power, the target compound that is captured by the adsorbent will dissolve in dichloromethane even through it cannot be eluted by water. Accordingly, almost simultaneously with the initial discharging of the emulsion from the trap column 8, the target compound will begin to be contained in the eluate.

The controller 30 estimates the period of time t1 from the initiation of the supply of dichloromethane until the emulsion begins to be discharged, and determines whether the elapsed time from the initiation of the supply of dichloromethane has reached the time t1 (Step S4). This period of time t1 is computed from the void volume within the trap column 8 (i.e. the volume of water present within the trap column 8 immediately before the introduction of dichloromethane is initiated) and the flow rate (0.5 mL/min) of dichloromethane supplied by the pump 7. Alternatively, the period of time t1 may be determined by an experiment or computed in advance by a user to be set through the operation unit 31.

After recognizing that the specified time t1 has elapsed from the initiation of the supply of dichloromethane, the controller 30 decreases the flow rate of the pump 7 to 0.1 mL/min (Step S5). At the same time, the controller 30 switches the two-way selector valve 12 from the disposal passage 14 to the preparative separation passage 13 to initiate the preparative separation of the emulsion (Step S6).

At the same time, the controller opens the on/off valve 16 to initiate the supply of nitrogen gas through the gas supply passage 15 (Step S7). Additionally, the controller 30 specifies a target temperature for the temperature regulator 21 and initiates the heating of the container rack 18 and thereby the heating of the collection containers 17 (Step S8). The target temperature may be approximately equal to or somewhat higher than the boiling point of dichloromethane, i.e. 40 to 45 degrees Celsius. The supply of nitrogen gas and the heating of the collection containers 17 may be initiated before the preparative separation process is initiated.

The operation performed in Step S5 in which the supply flow rate of the pump 7 has been decreased to 0.1 mL/min considerably decreases the amount of eluate per unit time exiting from the trap column 8, i.e. the emulsion with the target compound contained therein, which drips from the solution nozzle 13a via the preparative separation passage 13. Due to the closely located flow of gas ejected from the gas ejection nozzle 15a, the small amount of emulsion dripping into the collection container 17 does not directly fall but is broken into fine droplets and scattered around, as shown in FIG. 5. As stated earlier, the collection containers 17 are heated to a temperature that approximately equals the boiling point of dichloromethane. Therefore, when a small amount of fine droplet adheres to the inner circumferential wall or inner bottom wall of the collection container 17, most of the dichloromethane in the droplet immediately vaporizes. Compared to dichloromethane, water is less volatile and requires more time to vaporize. Therefore, water contained in the droplet may flow down the inner wall to deposit on the bottom of the container. The vaporization of water by heating is smoothly performed by reducing the amount of emulsion flowing into the collection container 17 per unit time as previously described until the water remaining in the collection container 17 completely vaporizes. In other words, by setting a low supply rate of the pump 7 per unit time for the period of time from the point in time when the emulsion begins to be collected until the water remaining in the collection container 17 completely vaporizes, the solvent in the eluate collected in the collection container 17 will be more efficiently vaporized, which can reduce the time required for the drying of the target compound. To further accelerate the vaporization of the solvent, it is also possible to powerfully supply the flow of gas at the water which has flowed down the inner wall and deposits on the bottom of the container.

Decreasing the supply flow rate suppresses the degree of muddling of the emulsion and decreases the percentage of water flowing into the collection container 17 in a given period of time. In this situation, it is possible that only dichloromethane remains incompletely vaporized on the inner wall of the collection container 17 and collected on the bottom of the container. Even if this occurs, the dichloromethane remaining on the bottom of the container can be efficiently vaporized because there is no water covering the upper side of the dichloromethane and preventing the vaporization of dichloromethane.

Setting a low supply flow rate per unit time from the point in time when the emulsion is discharged from the trap column 8 until it reaches the collection container 17 through the preparative separation passage 13 also brings about the following favorable effect. That is, if the target compound is soluble in dichloromethane and poorly-soluble in water, the target eluted in the dichloromethane deposits upon contact with water, and the deposit clogs the passage. Since the emulsion is a turbid liquid of water and an organic solvent (dichloromethane in this embodiment), decreasing the supply flow rate per unit time can suppress the degree of muddling of them in the emulsion. Consequently, setting a low supply flow rate per unit time of the pump 7 brings about the effect of suppressing the deposit of the target compound in the preparative separation passage 13.

Then the controller 30 judges whether the time after dichloromethane is begun to flow reaches a predetermined time t2 (Step S9). The time t2 is predetermined as the expected time length from the time when dichloromethane is begun to flow to the time when the water in the collection container 17 dries. When the controller 30 determines that the time t2 has elapsed, it returns the flow rate of the pump 7 to the original flow rate (0.5 mL/min) (Step S10).

Existence of water in the collection container 17, the preparative separation passage 13, and/or the column 8 is not desirable for collecting the target compound. Hence, temporarily halting the supply of dichloromethane after the emulsion is discharged into the collection container 17 from the column 8 seems to be an effective operation to vaporize the water.

However, with this method, the target compound remaining in the preparative separation passage 13 and in the column 8 will be dried during the vaporization of the water. After that, even though dichloromethane is passed through the column 8 and the preparative separation passage 13, the target compound cannot be sufficiently collected.

Given this factor, dichloromethane is continuously supplied in this embodiment. Since the supply flow rate is low (0.1 mL/min) and the dichloromethane immediately vaporizes, this supply of dichloromethane does not affect the drying operation of the target component or the vaporizing operation (or vaporizing time) of water.

Next, the controller 30 determines whether or not the elapsed time from the initiation of the supply of dichloromethane has reached the specified time t3 (Step S11). The time t3 is the period of time from the initiation of the supply of dichloromethane until the target component is completely eluted from the trap column 8. In the present embodiment, the period of time t3 is obtained by an experiment or computation in advance. After determining that the specified time t3 has elapsed, the controller 30 switches the two-way selector valve 12 to the disposal passage 14 (Step S12). Consequently, almost all the target component captured in the trap column 8 can be collected in the collection container 17.

At the same time, the controller 30 closes the on/off valve 16 of the gas supply passage 15 to halt the supply of nitrogen gas and halts the operation of the heater 19 (Step S13). Simultaneously, the controller 30 connects the supply passage 6 (port a) and the solvent solution 4 (port e) of the selector valve 5 so that the acetonitrile held in the solvent container 4 is supplied to the supply passage 6 via the pump 7 at 20 mL/min (Step S14). Consequently, the trap column 8 is washed and the solvent contained therein is replaced with acetonitrile, which is a solvent appropriate for rinsing the trap column 8, for the next analysis.

The controller 30 estimates the period of time t4 from the initiation of the supply of acetonitrile until the content in the trap column 8 is completely replaced with acetonitrile and determines whether or not the elapsed time from the initiation of the supply of acetonitrile has reached the time t4 (Step S15). The period of time t4 is computed from the void volume within the trap column 8 and the flow rate (20 mL/min) of acetonitrile supplied by the pump 7. The period of time t4 may be determined by an experiment or computed in advance by a user to be set through the operation unit 31.

After recognizing that the specified time t4 ha elapsed from the initiation of the supply of acetonitrile, the controller 30 halts the supply operation of the pump 7 (Step S16) to terminate the preparative separation/purification task.

It should be noted that the embodiment described thus far is merely an example of the present invention, and it is evident that any modification or addition made within the spirit of the present invention is allowed. For example, in the previous embodiment, the period of time for changing the supply flow rate of the pump 7 and the period of time for switching the two-way selector valve 12 from the disposal passage 14 to the preparative separation passage 13 (or vice versa) were obtained by a computation. These periods of time can be obtained by other method. For example, a turbidimeter capable of recognizing the degree of turbidity of the solution passing through the discharge passage 10 leading from the trap column 8 may be settled on the discharge passage 10. When this turbidimeter detects that the eluate from the trap column 8 has changed from water to the emulsion with dichloromethane, the controller 30 decreases the supply flow rate of the pump 7 to 0.1 mL/min, and switches the two-way selector valve 12 from the disposal passage 14 to the preparative separation passage 13 to initiate the preparative separation of the eluate containing the target.

In addition, the timing for changing the supply flow rate of the pump 7 and/or the timing for switching the two-way selector valve 12 from the disposal passage 14 to the preparative separation passage 13 (or vice versa) may be a little while before or after the time computed or estimated in the aforementioned manner. To this end, a setting means may be further provided to allow a user to set a time (e.g. several tens of seconds) for advancing or delaying the timing of the switch. Then, the timing of the switch is shifted by the period of time set by the setting means.

In the previously described embodiment, only one trap column 8 was used. However, a plurality of trap columns 8 may be used. That is, two or more trap columns with the same compound or different compounds captured therein are prepared in advance and set in the column rack 9. Then, a passage selection means (e.g. a valve) is provided so that one of these trap columns can be connected to the supply passage 6 and the disposal passage 14 to elute the compound from the selected trap column. In this manner, two or more compounds eluted from the plurality of trap columns can be individually collected in different collection containers.

Furthermore, in the previously described embodiment, the mobile phase in the trap column 8 was replaced with water and this water in turn was extruded by dichloromethane. In the case of using water or an aqueous solvent as the mobile phase itself, dichloromethane may be introduced to extrude the mobile phase from the trap column 8. The present invention can also be applied to this case.

In addition, in the previously described embodiment, a dichloromethane/methanol mixture was used as the second solvent and acetonitrile was used as the third solvent. The second and third solvents are not limited to them. A plurality of solvents each optimal for different target components may be prepared to appropriately select the optimal solvent by the passage selection means.

What is claimed is:

1. A preparative separation/purification system for passing a solution containing a target component through a trap column to capture the target component in the trap column and then passing a solvent having an elution capability through the trap column to elute the target component from the trap column and collect the target component, comprising:
    a) a holding means for holding the trap column to extend an internal passage of the trap column vertically with an inlet end thereof directed downwards and a discharge end thereof directed upwards;
    b) a liquid supply means for supplying a second solvent to the inlet end of the trap column, with the target component captured in the trap column held by the holding means, the second solvent having a low solubility to a first solvent remaining in the trap column and having a specific gravity greater than a specific gravity of the first solvent;
    c) a passage selection means for changing a passage configuration to selectively send a solution exiting from the discharge end of the trap column to either a collection passage leading to a collection container or a disposal passage leading to a disposal port;
    d) a passage control means for controlling the passage selection means to send the first solvent extruded from the discharge end of the trap column by a push of the second solvent to the disposal passage according to the action of supplying the second solvent to the trap column by the liquid supply means, and to send the solution with the second solvent contained therein to the collection passage at a timing when the solution exits from the discharge end of the trap column; and
    e) a flow rate control means for controlling the liquid supply means to supply the second solvent at a first supply flow rate when the first solvent is sent to the disposal passage from the discharge end of the trap column, and to supply the second solvent at a second supply flow rate which is lower than the first supply flow rate when the solution with the second solvent contained therein is sent to the collection passage from the discharge end of the trap column;
    wherein the passage control means is further configured to control the passage selection means to send an emulsion containing the target component in the second solvent, to the collection passage from the discharge end of the trap column.

2. The preparative separation/purification system according to claim 1, further comprising:
    f) a computation means for computing a period of time from a point in time when the second solvent begins to be sent to the trap column until the solution with the second solvent contained therein begins to be discharged from the discharge end of the trap column, the period of time being computed from an internal volume of the trap column and the first supply flow rate,
    wherein the passage control means is configured to control the passage selection means, when the period of time computed by the computation means has elapsed, in such a manner that the solution with the second solvent contained therein exiting from the discharge end of the trap column is sent to the collection passage.

3. The preparative separation/purification system according to claim 1, further comprising:
    g) a collection passage switching time setting means for allowing a user to set a period of time from a point in time when the second solvent begins to be sent to the trap column until the solution with the second solvent contained therein begins to be discharged from the discharge end of the trap column,
    wherein the passage control means is configured to control the passage selection means, when the period of time set by the collection passage switching time setting means has elapsed, in such a manner that the solution with the second solvent contained therein exiting from the discharge end of the trap column is sent to the collection passage.

4. The preparative separation/purification system according to claim 1, further comprising:
    h) a discharged solution discrimination means for determining whether or not the solution discharged from the discharge end of the trap column contains the second solvent,
    wherein the passage control means is configured to control the passage selection means, when the discharged solvent discrimination means has determined that the discharged solution contains the second solvent, in such a manner that the solution with the second solvent contained therein exiting from the discharge end of the trap column is sent to the collection passage.

5. The preparative separation/purification system according to claim 1, further comprising:
    i) a disposal passage switching time setting means for allowing a user to set a period of time after the elapse of which the passage selection means changes the passage configuration in order to change the passage of the solvent from the collection passage to the disposal passage after the second solvent exiting from the trap column is sent to the collection passage,
    wherein the passage control means is configured to control the passage selection means, when the period of time set by the disposal passage switching time setting means has elapsed, in such a manner that the solution exiting from the trap column is sent to the disposal passage.

6. The preparative separation/purification system according to claim 5, wherein the disposal passage switching time setting means is configured to set a period of time required for the target component captured in the trap column to be completely eluted by the second solvent.

7. The preparative separation/purification system according to claim 5, wherein the disposal passage switching time setting means is configured to set a period of time required for a drying of the target component contained in the solution collected in the collection container to be completed.

8. The preparative separation/purification system according to claim 1, further comprising:
- j) a heater for heating the collection container; and
- k) a gas supplier for forming a flow of gas to scatter the discharged solution which is dripped or flowed into the collection container.

9. The preparative separation/purification system according to claim 1, wherein:
- the liquid supply means for supplying either the second solvent or a third solvent to the inlet end of the trap column, and the preparative separation/purification system further comprises:
- l) a solvent selection means for changing a kind of a solution supplied by the liquid supply means to either the second solvent or the third solvent for washing the trap column;
- m) a third solvent switching time setting means for allowing a user to set a period of time for the solvent selection means to change the solvent to the third solvent from the second solvent; and
- n) a solvent control means for controlling the solvent selection means, when the period of time set by the third solvent switching time setting means has elapsed, to change the solvent supplied to the liquid supply means to the third solvent from the second solvent.

* * * * *